United States Patent [19]
Malchesky

[11] Patent Number: 5,833,935
[45] Date of Patent: *Nov. 10, 1998

[54] MICROBIAL DECONTAMINATION SYSTEM WITH COMPONENTS POROUS TO ANTI-MICROBIAL FLUIDS

[75] Inventor: Paul S. Malchesky, Painesville Twp., Ohio

[73] Assignee: Steris Corporation, Mentor, Ohio

[ * ] Notice: The term of this patent shall not extend beyond the expiration date of Pat. No. 5,552,115.

[21] Appl. No.: 660,511

[22] Filed: Jun. 7, 1996

Related U.S. Application Data

[62] Division of Ser. No. 187,855, Jan. 28, 1994, Pat. No. 5,552,115.

[51] Int. Cl.⁶ ........................................................ A61L 2/16
[52] U.S. Cl. ........................... 422/300; 422/28; 206/210; 206/370; 206/438
[58] Field of Search .................................. 422/300, 301, 422/28; 206/370, 438, 210

[56] References Cited

U.S. PATENT DOCUMENTS

| | | | |
|---|---|---|---|
| 3,877,570 | 4/1975 | Barry | 206/63.3 |
| 3,950,251 | 4/1976 | Hiller | 210/232 |
| 4,024,304 | 5/1977 | Smock et al. | 427/316 |
| 4,126,126 | 11/1978 | Bare et al. | 128/2 |

(List continued on next page.)

FOREIGN PATENT DOCUMENTS

| | | |
|---|---|---|
| 283011 | 9/1988 | European Pat. Off. . |
| 395296 | 10/1990 | European Pat. Off. . |
| 397352 | 11/1990 | European Pat. Off. . |
| 507461 | 10/1992 | European Pat. Off. . |

(List continued on next page.)

OTHER PUBLICATIONS

"Disinfection and Sterilization", McCulloch, 1945, pp. 91–93.
Porex Technologies Advertising Brochure, 1992.
Instruction Manual, pp. 413–422 of STERIS (Nov. 1992).
Corrosion Protection of Tubing by a Fluidized Sintered Plstic Coating vol. 89, No. 10, Sec. 042, Abs. No. 07640 (abstract only).

(List continued on next page.)

Primary Examiner—Robert J. Warden
Assistant Examiner—E. Leigh McKane
Attorney, Agent, or Firm—Fay, Sharpe, Beall, Fagan, Minnich & McKee

[57] ABSTRACT

A countertop decontamination unit (A) has a decontamination chamber (10) for receiving a tray or module (C) which contains items to be sterilized, disinfected, or otherwise microbially decontaminated. The tray or walls of the decontamination chamber itself provide fluid outlets from which an anti-microbial solution is conveyed through tubing (76) to fittings (78). A pump (20) recirculates the anti-microbial fluid. The fittings include a porous sleeve (80, 92) which is received in firm frictional connection with an annular surface of a bore, nipple, or coupler mechanism of the item (86) to be sterilized. The porous sleeve is preferably elastomeric when used for frictional interconnections, but may be rigid when used with threaded or other standardized connectors. The porous sleeve has a porosity of 3 microns or more, sufficient that the anti-microbial fluid penetrates through the porous portion and contacts the immediately contiguous and abutting annular surface. The porous member permits sufficient quantities of solution to contact these surfaces to assure they are microbially decontaminated. Associated surfaces that contact the item and can potentially trap microbes are also constructed of porous material. Other associated porous structures include porous closures, such as plugs (124, 160) or caps (120, 122) which close some of the access ports to the interior passages of endoscopes, item retainers (68), a bottom wall portion (62), other surfaces of the item (174), and the like.

10 Claims, 8 Drawing Sheets

U.S. PATENT DOCUMENTS

| | | | |
|---|---|---|---|
| 4,127,732 | 11/1978 | Bleha et al. | 560/221 |
| 4,135,868 | 1/1979 | Schainholz | 422/300 X |
| 4,227,527 | 10/1980 | De Frank et al. | 128/214 |
| 4,273,142 | 6/1981 | Swanson et al. | 131/339 |
| 4,299,244 | 11/1981 | Hirai | 134/102 |
| 4,329,814 | 5/1982 | Blicha | 47/79 |
| 4,393,521 | 7/1983 | Jones | 205/600 |
| 4,434,250 | 2/1984 | Kessler | 521/64 |
| 4,798,292 | 1/1989 | Hauze | 422/300 X |
| 4,892,706 | 1/1990 | Kralovic et al. | 422/28 |
| 4,936,700 | 6/1990 | Morris | 401/196 |
| 4,976,922 | 12/1990 | Chippett et al. | 422/34 |
| 5,051,484 | 9/1991 | Sasaki et al. | |
| 5,064,541 | 11/1991 | Jeng et al. | 210/767 |
| 5,071,346 | 12/1991 | Domaas | 422/300 X |
| 5,077,008 | 12/1991 | Kralovic et al. | 422/37 |
| 5,084,251 | 1/1992 | Thomas | 422/300 |
| 5,085,773 | 2/1992 | Danowski | 210/446 |
| 5,120,512 | 6/1992 | Matsuda | 422/298 |
| 5,133,864 | 7/1992 | Vaughn et al. | 210/437 |
| 5,137,684 | 8/1992 | Cantrell | 422/300 X |
| 5,152,808 | 10/1992 | Blok | 47/59 |
| 5,174,956 | 12/1992 | Konishi et al. | 422/26 |
| 5,176,833 | 1/1993 | Vaughn et al. | |
| 5,185,169 | 2/1993 | Yamamoto | 427/246 |
| 5,190,659 | 3/1993 | Wang et al. | 210/663 |
| 5,281,391 | 1/1994 | Hanson et al. | 422/292 X |
| 5,433,930 | 7/1995 | Taschner | 422/300 |
| 5,534,221 | 7/1996 | Hillebrenner et al. | 422/297 X |
| 5,552,115 | 9/1996 | Malchesky | 422/300 X |

FOREIGN PATENT DOCUMENTS

| | | |
|---|---|---|
| 4106696 | 9/1991 | Germany . |
| 4110175 | 10/1991 | Germany . |
| 300170 | 5/1992 | Germany . |
| 58-124427 | 7/1983 | Japan . |
| 58-180130 | 10/1983 | Japan . |
| 1-69502 | 5/1989 | Japan . |
| 91-68434 | 3/1991 | Japan . |
| 91-86730 | 4/1991 | Japan . |
| 91-93842 | 4/1991 | Japan . |
| 91-168204 | 7/1991 | Japan . |
| 91-175028 | 8/1991 | Japan . |
| 91-213586 | 9/1991 | Japan . |
| 91-265634 | 11/1991 | Japan . |
| 91-290446 | 12/1991 | Japan . |
| 92-18925 | 1/1992 | Japan . |
| 92-50246 | 2/1992 | Japan . |
| 92-53843 | 2/1992 | Japan . |
| 92-71603 | 3/1992 | Japan . |
| 92-9336 | 3/1992 | Japan . |
| 92-168131 | 6/1992 | Japan . |
| 92-180699 | 6/1992 | Japan . |
| 92-182124 | 7/1992 | Japan . |
| 92-209636 | 7/1992 | Japan . |
| 4-312440 | 11/1992 | Japan . |
| 4-336027 | 11/1992 | Japan . |
| 2182105 | 5/1987 | United Kingdom . |
| 2219246 | 12/1988 | United Kingdom . |

OTHER PUBLICATIONS

"Porous PE Tubes Promote Research, Save Time, Money", RPA 90–25–408759 Plast. Des. Forum 1990 15, No. 6, pp. 32–33. (abstract only).

"Formula For Happy Plants", RPA 75–08–50992 Du Pont Mag. 1975, 69, No. 3, pp. 9–11 (abstract only).

"Duont Viaflo Porous Plastic Irrigation Tubing", RPA 75–12–3550 Bergman, et al., Proc. 11th Natl. Agri. Plast. Conf. Nov. 1973, pp. 26–34 (abs.).

"Piping Elements Lines with Fluorinated Plastics. Chemical Resistant", FLD 0199418 X, Ind. Anz. v. 103, No. 54, Aug. 1986, pp. 22–23 (abstrct only).

"Polynorbornene: The Porous Polymer", Ohm, FLD 0100995FS Chemtech, Vo. 10, No. 3, Mar. 1980, pp. 183–187 (abstract only).

"Application of Perm–Porous–Metal Plastics Composites (PMP Composites) for Flow Bottoms", Selig., FLD0054580SL, Pneumotransport 4, 4th Int'l Conf. on the Pneumatic Transport of Solids in Pipes, Jun. 1978; vol. 1, pp. E2–13–22 (abs.).

"The Use of 'FRP–1' Porous Plastic in Construction Operations and Structures of the UST–ILIM Hydroelectric Station", Kepalas, et al., Gidrotekh. Stroit., vol. 9, 1977, pp. 11–14 (abstract only).

"The Physical–Mechanical Properties of Ftorlon (Fluoroplastic) Filter Materials", Kuvalzin, et al., Plasticheskie Massey, 6, 1976, pp. 49–50 (abs.).

"Nylasint Pore System: Reservoir or Sink. Interim Report" Dormant, et al. Aerospace Corp. El Segundo CA, Jul. 195; 25pp. (abstract only).

"Porous Plastic Silencers Hush Pneumatic Presses" Engr. vol. 237, No. 6136 p. 23, Oct. 1973 (abstract only).

"New Low Cost Sintered Plastic", Eng. News (55) Sep. 89, p. 6 (abstract).

"Solving Fluid–Flow Control Problems With Porous Plastics", Wolbrum, Med. Device Technol. vol. 4, No. Jan.–Feb. 1993, pp. 18–20 (abstract only).

"Permeability of (3H) Water Across a Porous Polymer Matrix Used As Rate–Limiting Shell in Compression- –Coated Tablets", Ritschel, et al. J. Controlled Release, vol. 12, No. Apr. 1990, pp. 97–102 (abstract only).

"Selective Retention by Porous Polymer Adsorbents: Application to Formaldehyde Determination", Frankel, et al., Anal. Chem. vol. 44, No. 12/92, pp. 2401–2402.

"Sustained–Release Formulation of Prednisolone Administered Orally to Man", D'Arcy, et al., J. Pharm. Sci., vol. 60, No. Jul. 71, pp. 1028–1033 (abs.).

"Porous Plastic Fine Particles", New. Mat./Jap. Feb. 1992, p. 11.

"Open Cell Porous Plastics For Use in Environmental Protection, Filtration Technology and Other Areas", Borocz, Muanyag es Gumi 1990, 27 No. 10 p. 2–93–8.

"Porous Polymer Bared", Jap. Chem. Week 1989 30, No. 1537, Sep. 1989.

"Porous Resin Cleans Fluoride From Waste Wate", New Mat./Jap. 1989 6 No. 10, Oct. 1989, pp. 12–3.

"Slip Casting of Silicon Nitride and Mechanical Properties of Sintered Body II Vacuum–Pressure Assisted Slip Casting of Silicon Nitride Powder Produced by Direct Nitridation", Ohshima, et al., Nippon Seramikkusu Kyokai Gakujutsu Ronbunshi (Journal of the Ceramic Society of Japan) 100 Aug. 1992, pp. 1032–1037.

"Synthesis and Characterization of Crosslinked Polymers IV. Flexibility of the Polymer Chain of Crosslinked Polymers and Swelling", T. Yamamizu, et al. Kobunshi Ronbunshu 47, (6) May 1990, pp. 475–482.

"Development of a Molding Technique by Vacuum Pressure Casting Method: Strengthening of High Purity Alumina", H. Mizuta, et al. Met. Technol. (Jpn.) 59, (6) 1989 pp. 14–19.

"Plastics in Engineering", M. Myers, S. Afr. Mech. Eng. 38, (8) Aug. 1988 pp. 438–439, 442–443, 445–446.

"New Speciality Plastics", W.C. Shumay, Adv. Mater. Process. Inc. Met. Prog. 134, (4), Oct. 1988, pp. 46–49.

"Pore Structure of Porous Polymers by Different Methods (Trans)", L. Belyakova Colloid J. USSR 49 (5) Sep.–Oct. 1987, pp. 747–751.

"Invest. of the Structure of Pores of Porous Polymers by Different Methods", Blyakova, et al. Kolloidn. Zh. 49 (5) 1987, pp. 847–851.

"Medical Applications Demonstrate the Importance of Plastics", G. Parkinson, Rev. Plast. Mod. 60, No. 412, Oct. 1990, p. 6–03–6.

"Porex Technologies Acquires German Processing Concern", R. Shinn, Plast. News (USA) 1991 3 No. 1, Mar. 4, 1991, p. 1/20.

"Porex Technologies", 1983 Fairburn, GA 1983 p. 28.

"Porous PE Upgrades Water Filter", Mod. Plast. Int. 1981 11, No. 8, Aug. 1981, p. 46.

"Porous HDPE Quiets Noisy Blasts", Plast. World 1980 38, No. 6, Jun. 1980, p. 31.

"Water Purifier's Porous Polyethylene Filter Signals When It's Time For A Change", Moore, Plast. Des. Process. 1980 20 No. 2, 1980 pp. 18–19.

"Porous Plastic Filter Changes Colour As It Removes Particulates", Mat. Engn. 1979 89, No. 1, Jan. 1979, p. 11.

"Microporous Plastics Promise A New Era in Filtration", F. Conway, Plast. Eng. 1975, 31 No. 2, Feb. 1975, pp. 20–23.

"Functionalization and Chelating Properties of a Porous Polymer Derived From Vinylamine", Tbal, et al. Eur. Polym. J., 1992, vol. 28, Iss. 6, pp. 671–679.

"On the Deformational Characteristics of Porous Polymeri Tubes", M. Islam J. Appl. Polym. Sci, 1992, vol. 44, Iss. 11, pp. 1899–1903.

"Transport of Macromolecules in Porous Media", M. Sahimi, J. Chem. Phys., 1992, vol. 96, ISS. 6, pp. 4718–4728.

"Interfacial Adsorption of Solvents in a Porous Polymer Resin: A Carbon–13 Spin–Echo and ESR Study", Chachaty, et al., J. Phys. Chem. vol. 95, Iss. 16, pp. 6058–6060.

"Thermodynamics of Formation of Porous Polymeric Membranes From Solutions", S. MAtsuda, Polym. J. 1991, vol. 23, ISS. 5, pp. 435–444.

"Observations and Analysis of Geomatrical Changes in Sintered Polymer Particles on the Example of Polystyrene", Polimery 35 (3), Mar. 1990; pp. 79–81.

"Volume Change of Porous Crosslinked Polystyrenes and Retention of Pore Structures Synthesis and Characterization of Crosslinked Polymers III", K. Takeda, et al. Kobunshi Ronbunshu 46 (10), 1989, pp. 623–633.

"Influence of a Spacer on the Kinetics of Reduction of Carbonyl Compounds With Porous Borohydride Exchange Resin", M. Bacquet, et al., React. Polym. 1992, 18, No. 3, Dec. 1992, pp. 185–190.

"Hoover First For Porvair", Plast. Rubb. Wkly, 1992, No. 1466, Dec. 19, 1992, p. 5.

"Porous Polymer Implants for Repair of Full–Thickness Defects of Articular Cartilage. Experimental Study in Rabbit and Dog", J. Klompmaker, et al. Biomaterials 1992, 13 No. 9, pp. 625–634.

"PBI Bearing Venture Set", Chem. Mark. Reporter 242, No. 1, Jul. 6, 1996; p. 7.

"Generation of Porous Polymer Surfaces by Solvent–Nonsolvent Treatment", J. Cheng, et al, J. Appl. Polym. Sci. 45, No. 3, May 25, 1992, pp. 377–386.

"Binding Catalytic Sites to the Surface on Porous Polymers and Some Catalytic Applications", E. Ruckenstein, et al. Chem of MAt. 4, No. 1, Jan./Feb. 1992 pp. 122–127.

"Dimerisation of Ethylene Catalysed By a Nickel Catalyst Supported on Porous Polymers", J–C Carlu, et al., React. Polym. 1990 13, No. 1/2, Sep. 1990, pp. 153–160.

Fischer–Tropsch Synthesis Catalysed by Iron Catalyst Supported on Porous Polymers (Styrene–Divinylbenzene and 4–Vinylpyridine–Divinylbenzene Copolymers) II. Catalytic Results J–C Carlu, et al. React. Polym. 1990, 12 No. 2 Apr. 1990, pp. 187–192.

"MDHS 50. Methods for the Determination of Hazardous Substabces. Benzene in Air. Laboratory Method Using Porous Polymer Diffusion Samplers, Thermal Desorption and Gas Chromatography", 1985 London UK Health & Safety Executive.

"MDHS 55. Acrylonitrile in Air. Laboratory Method Using Porous Polymer Diffusion Samplers, Thermal Desorption and Gas Chromatography", 1986 London UK Health & Safety Executive.

"MDHS 43. Methods for the Determination of Hazardous Substances. Styrene in Air. Laboratory Method Using Porous Polymer Diffusive Samplers, Thermal Desorption and Gas Chromatography", 1985 London UK Health & Safety Executive.

"MDHS 31. Methods for the Determination of Hazardous Substances. Styrene in Air. Laboratory Method Using Porous Polymer Adsorbent Tubes, Thermal Desorption and Gas Chromatography", 1989 London UK Health & Safety Executive.

"Synthesis of Molecular Organometallic Composites: Polymerisation of Vinylferrocene in a Porous Polymer Matrix", R. Arshady, et al. Adv. Mat. 1990 2, No. 9, pp. 412–414.

"Sintercon Sintered Plastic Filters", Wrexham c. 1988 pp. p. 4, Advanced Filtration Ltd.

"Characteristics of Porous Polymer Composite Columns Prepared by Radiation Cast–Polymerisation", M. Kumakura, J. Mat. Sci. Lett. 1989, 24 No. 5, May 1989 pp. 1809–1813.

"Role of Polymer Matrix Structure and Interparticle Interactions in Diffusion–Limited Drug Release", A. Balazo, et al., Poly. Sci. and Tech. vol. 32, 6S (13) Plenum Press, 1985, pp. 87–101.

"Elastic Properties of Porous Thermosetting Polymers" K. Phani, et al., J. Mat. Sci. 1987 22 No. 10, Oct. 87, pp. 3453–3458.

"Hogs Head For Industrial Spills", Plast. Rubb. Wkly. 1987 No. 1205, Sep. 19, 1987, p. 21.

"Toxic Organic Compound Recoveries From 2, 6–Diphenyl–p–Phenylene Oxide Porous Polymer Uisng Supercritical Carbon Dioxide and Thermal Desorption Methods", J. Raymer, Analyst. Chem. 1987 59 no. 7, Apr. 1, 1987, pp. 1043–1048.

"Vyon. A Versatile and Remarkable Porous Plastic For Use in Industry", v. 1986, p. 8.

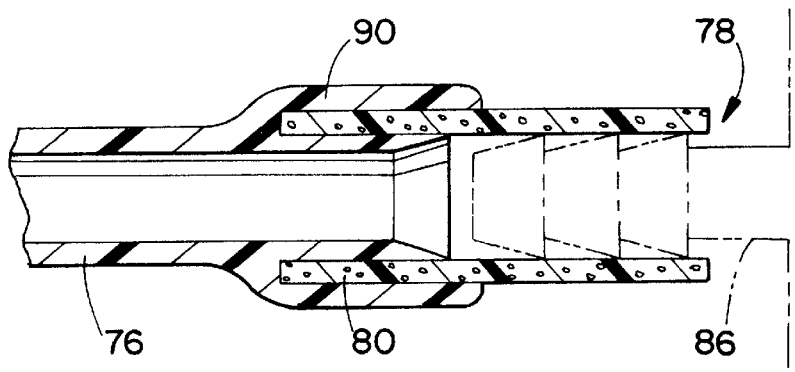
FIG. 6
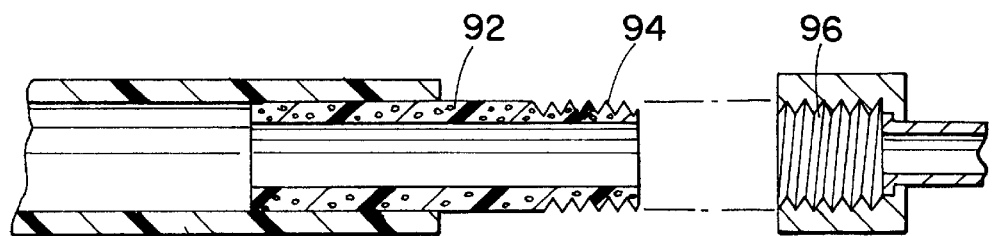
FIG. 7
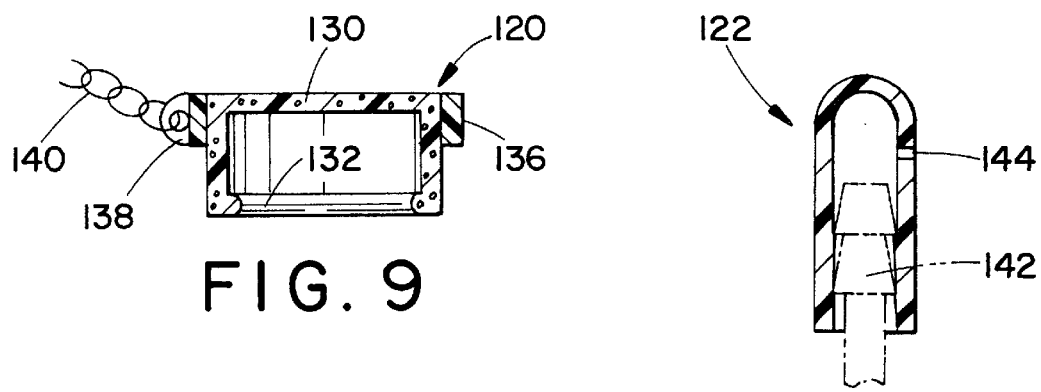
FIG. 9
FIG. 10
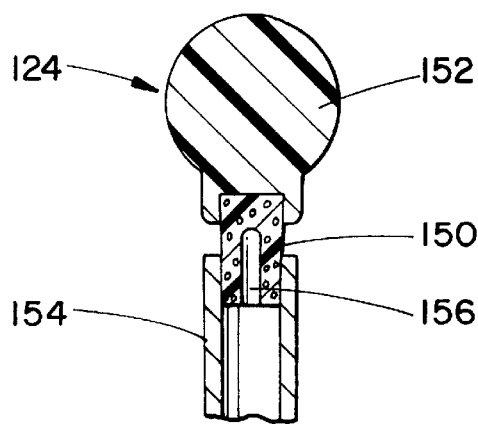
FIG. 11
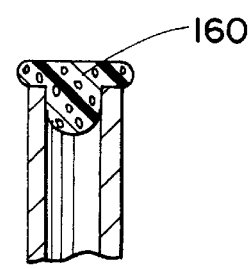
FIG. 12

MICROBIAL DECONTAMINATION SYSTEM WITH COMPONENTS POROUS TO ANTI-MICROBIAL FLUIDS

This application is a divisional of U.S. application Ser. No. 08/187,855, filed Jan. 28, 1994, now U.S. Pat. No. 5,552,115.

BACKGROUND OF THE INVENTION

The present invention relates to the decontamination art. It finds particular application in conjunction with sterilizing instruments and equipment which contain or potentially contain biological contaminants, such as medical, dental, veterinary, and mortuary instruments and equipment and will be described with particular reference thereto. It is to be appreciated, however, that the invention is also applicable to a wide variety of technologies in which contamination removing or other treating reagents in liquid, gas, or vapor form are blocked by surfaces, connectors, or other treating agent impermeable structures from reaching adjacent surfaces.

Decontamination connotes the elimination, killing, or removal of hazardous or unwanted materials, such as bacteria, mold spores, other pathogenic life forms, radioactive dust, and the like. Disinfection connotes the absence of pathogenic life forms. Sterilization connotes the absence of all detectable life forms, whether pathogenic or not. Thus, a sterilized instrument is also disinfected.

Heretofore, medical, dental, and surgical equipment and instruments have often been sterilized in a steam autoclave. Autoclaves kill life forms with a combination of high temperature and pressure. However, steam autoclaves have several drawbacks. The high temperature pressure vessels tend to be bulky and heavy. The high temperature and pressure tends to curtail the useful life of the endoscopes, rubber and plastic devices, lenses, bearings, portions of devices made of polymeric materials, and the like. Moreover, the autoclave sterilizing and cool down cycle is sufficiently long, that multiple sets of the medical, dental, or surgical instruments are commonly required.

Instruments which cannot withstand the pressure or temperature of the oven autoclave are often sterilized with ethylene oxide gas, particularly in larger medical facilities or hospitals. However, the ethylene oxide sterilization technique also has several drawbacks. First, the ethylene oxide sterilization cycle is even longer than the steam autoclave cycle. Another drawback is that ethylene oxide sterilization is sufficiently sophisticated that trained technicians are commonly required, making it unsuitable for physician and dental offices and for most smaller medical facilities. Yet another drawback is that some medical, surgical, and dental equipment can not be sterilized with ethylene oxide gas.

Anti-microbial fluid disinfection systems have also been utilized for equipment which could not withstand the high temperatures of steam sterilization or long cycle times of ethylene oxide. Commonly, a technician mixes a liquid disinfectant composition and manually immerses the items to be decontaminated. The high degree of manual labor introduces numerous uncontrolled and unreported variables into the disinfection process. There are quality assurance problems with the weakening of the disinfectants due to aging on the shelf, technician error in the mixing of disinfectants, technician error in the control of the immersion times, technician error between immersion and the rinsing of residue, technician error in the rinsing of the residue, exposure to the ambient atmosphere or other not yet disinfected instruments after the rinsing step, and the like.

Some medical items, such as endoscopes, have elongated tubular portions and internal bores. To assure that the internal passages are sterilized, the sterilant is normally pumped through a flexible connector or hose which has an elastomeric fitting on the end. The elastomeric fitting is commonly compression fit into an access port in the bore or stretched over an associated fitting. The elastomeric connector is manufactured of a material with sufficient resiliency that it is frictionally held securely in or around the fitting securely and does not disconnect under the pressure of the pumped sterilant fluid, whether liquid or gaseous.

In some instruments, particularly some type of endoscopes, there are branches in the bores. The branches have different diameters and access to the incoming sterilant. In some instruments, some of the branches tend to receive little or none of the pumped sterilant fluid. To redistribute the sterilant through these sterilant starved bores, plugs or caps close the bores which receive too high a percentage of the sterilant flow. To allow limited flow through the plugged bore, in some cases the plug, cap, or restrictor has a small diameter hole to allow limited sterilant flow. The plugs or caps are again constructed of a resilient polymeric material which are frictionally anchored by their elasticity into the bore or around an associated fitting.

In some applications, the connector at the end of the hose is configured of a non-elastomeric material, such as metal or hard plastic and threaded or otherwise fitted with the same connectors as the item whose internal passages are to be sterilized. This enabled the hose to be threadedly or otherwise securely connected with the item to be sterilized.

Liquid and gaseous anti-microbial systems can kill microbes on all surfaces that the anti-microbial fluid, liquid, or gas can reach. When a connector engages a contaminated surface, there is a potential for a portion of the surface to be shielded from the anti-microbial fluid, liquid, or gas. As the potential for contaminates to avoid contact by the anti-microbial fluid increases, the potential for microbes to survive the decontamination process increases.

The present invention provides a new and improved method and apparatus which eliminates the potential for the pockets of non-fluid contact.

SUMMARY OF THE INVENTION

In accordance with one aspect of the present invention, an improvement is provided for a microbial decontamination system for killing microbes on surfaces of an item with an anti-microbial fluid. At least one of the item surfaces contacts an associated surface raising the possibility that microbes might be trapped therebetween. An improvement comprises providing the associated surface with a porous portion in contact with the item surface. The porous portion is sufficiently porous that the anti-microbial fluid penetrates therethrough and kills the microbes on the item surface.

In accordance with a more limited aspect of the present invention, the associated surface is a surface of one of a fitting, a closure, a cap, a plug, a support surface, a retaining member, a spring clamp, and another portion of the item.

In accordance with another aspect of the present invention, an anti-microbial decontamination system is provided. The system includes a reservoir for receiving an item having at least one internal passage to be microbially decontaminated. The reservoir further receives and holds sufficient anti-microbial fluid to immerse the item. A pumping means pumps the anti-microbial fluid to a porous fitting. The porous fitting is selectively interconnected with a port to the interior passage of the item such that the pumping means pumps the anti-microbial fluid through the porous fitting into and through the internal passage.

In accordance with another aspect of the present invention, a microbial decontamination system is provided for microbially decontaminating interior passages of an item. A pumping means pumps an anti-microbial fluid through the interior passages and out access ports. A porous closure closes at least one of the access ports. The porous closure is mounted in firm frictional contact with a surface region of the item adjacent the port. The porous closure is sufficiently porous that the anti-microbial fluid penetrates through the porous closure to the frictionally contacted surface region and microbially decontaminates the surface region.

In accordance with another aspect of the present invention, a microbial decontamination system is provided. The microbial decontamination system includes a module for holding an item to be microbially decontaminated. The module includes an anti-microbial fluid inlet and an outlet. An ambient microbe blocking means prevents airborne microbes from entering the inlet and outlet. A porous structure is provided on which the item is supported. The pumping means pumps the anti-microbial fluid to the module inlet. The porous structure is permeable to the anti-microbial fluid such that the anti-microbial fluid penetrates the porous structure and reaches the surface item that contacts the porous structure.

In accordance with another aspect of the present invention, a microbial decontamination system is provided. The system includes a water inlet, a drain outlet, a decontamination region for receiving items to be microbially decontaminated, an anti-microbial solution mixing region, fluid flow paths among the inlet, the decontamination region, the mixing region, a rinse fluid filter, and a drain outlet, a fluid circulating means for circulating fluid through the flow paths, at least one tubular member in fluid communication with the decontamination region and connected with the fluid circulating means, and a fitting means. The fitting means is selectively interconnected with a port extending into an internal passage of an item to be microbially decontaminated. The fitting means is connected with the item to be microbially decontaminated in frictional communication with an immediately contiguous portion adjacent the port. The fluid fitting means includes a means for providing anti-microbial fluid to an interface between the fitting means and the immediately contiguous surface portion such that the immediately contiguous surface portion is microbially decontaminated.

In accordance with another aspect of the present invention, a porous fitting is provided. A tubular porous portion is received in intimate frictional contact with an annular surface region around a port in fluid communication with an internal region of an item to be microbially decontaminated. The tubular porous sleeve portion is sufficiently permeable to an anti-microbial fluid that the anti-microbial fluid penetrates the porous tube portion and microbially decontaminates the annular surface. In this manner, microbes are not trapped between the fitting and the annular surface.

In accordance with another aspect of the present invention, a method of killing microbes on surfaces of an item with an anti-microbial fluid is provided. A porous material is disposed against one of the surfaces of the item. The porous material and other surfaces of the item contact the anti-microbial fluid. The anti-microbial fluid is further caused to penetrate the porous material and contact the surface of the item disposed against it.

In accordance with another aspect of the present invention, a method of microbially decontaminating an item is provided. A porous fitting is connected into firm frictional contact with a surface adjacent port which provides access to an interior of the item. A microbial decontamination fluid is circulated through the porous fitting into the interior microbially decontaminating the interior. The porous fitting has sufficient porosity that the anti-microbial fluid penetrates through the porous fitting to the frictionally contacted surface adjacent the port microbially decontaminating such surface.

One advantage of the present invention is that it eliminates a source of potential microbial contamination.

Another advantage of the present invention is that it permits sterilant and disinfectant contact with medical instrument surfaces in contact with the fitting or other associated surfaces to sterilize or disinfect such surfaces.

Another advantage of the present invention is that it permits a sufficient flow of air, liquid, and gaseous anti-microbial agents through the fitting to allow sterilant and disinfectant to fill an area around the attachment and prevent air locks in dead legs which terminate with the fitting.

Another advantage of the present invention is that it enables anti-microbial agent residue to be removed, such as by rinsing or degassing.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 6 is a cross-sectional view of another embodiment of a fitting in accordance with the present invention;

FIG. 7 is a cross-sectional view of yet another embodiment of a fitting in accordance with the present invention;

FIG. 9 is a detailed cross-sectional view of cap 120 of FIG. 8B;

FIG. 10 is a cross-sectional view of a porous cap 122 of FIG. 8C;

FIG. 11 is a cross-sectional view of a plug in accordance with the present invention;

FIG. 12 is a cross-sectional view of an alternate embodiment of a plug in accordance with the present invention;

DETAILED DESCRIPTION OF THE PREFERRED EMBODIMENTS

Figure 1:
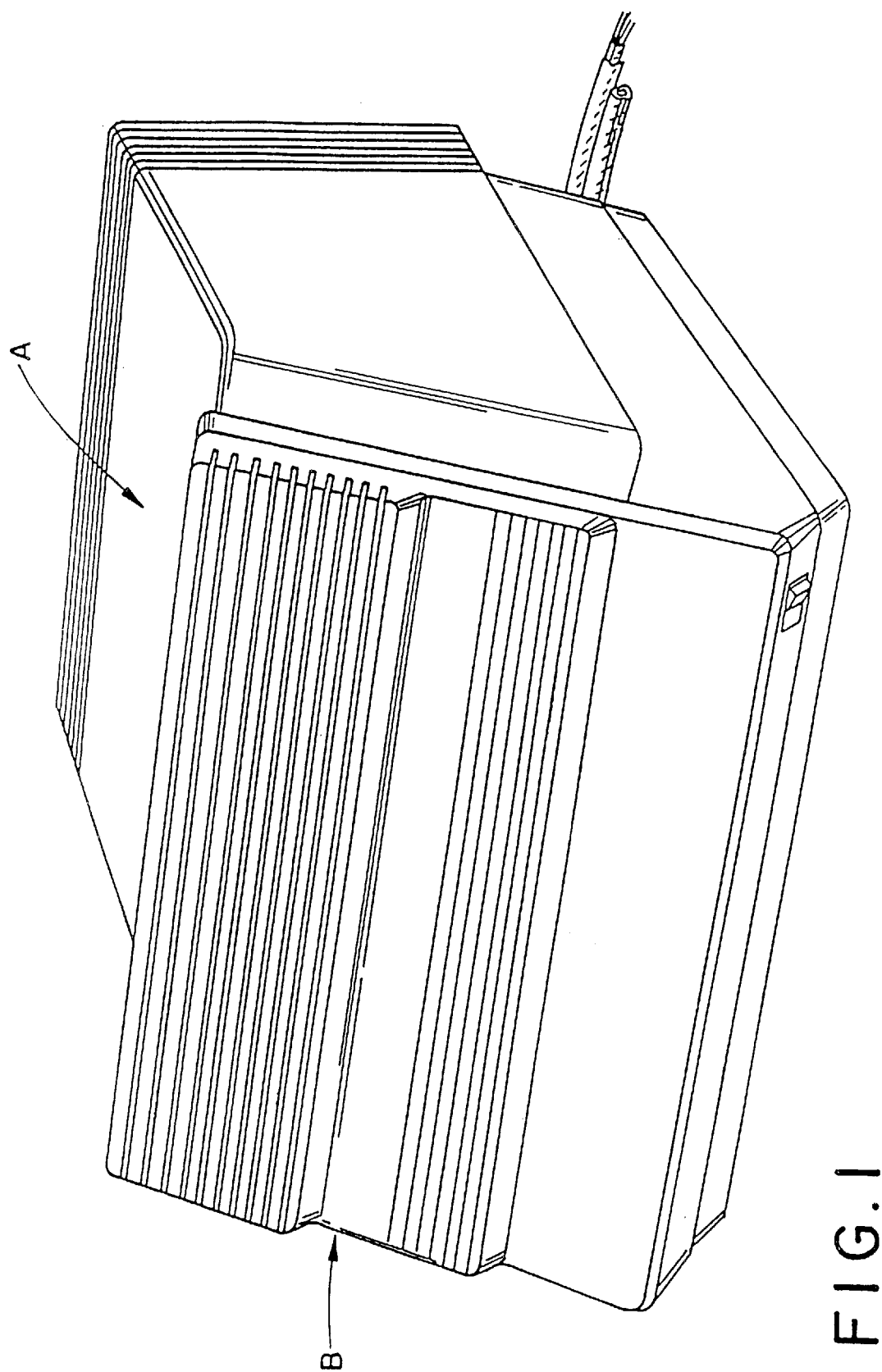
FIG. 1 is an exterior view of a countertop decontamination unit.
Figure 2:
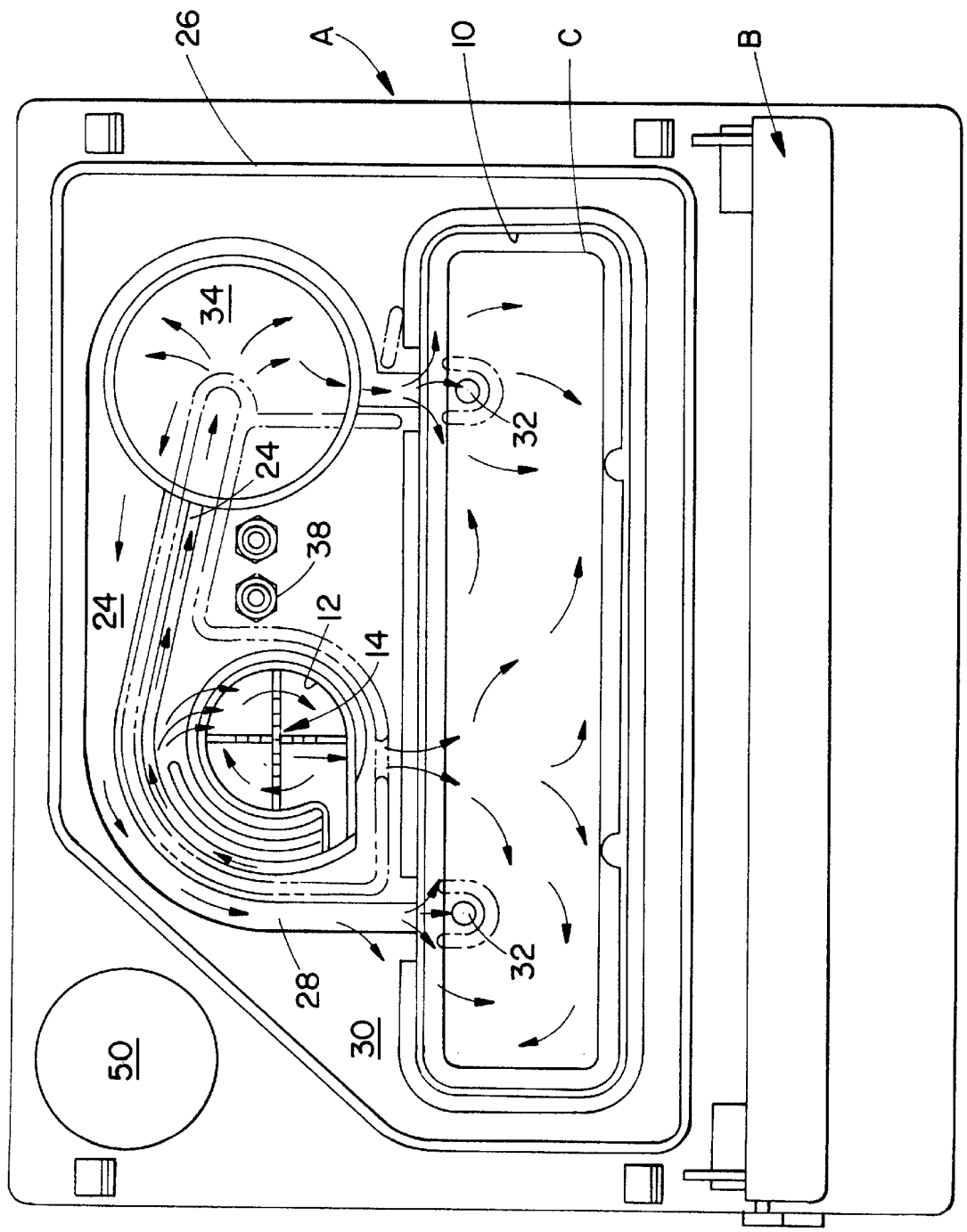
FIG. 2 is a front view of the decontamination unit with the door open and an instrument carrying tray or module received in the decontamination region.
Figure 3:
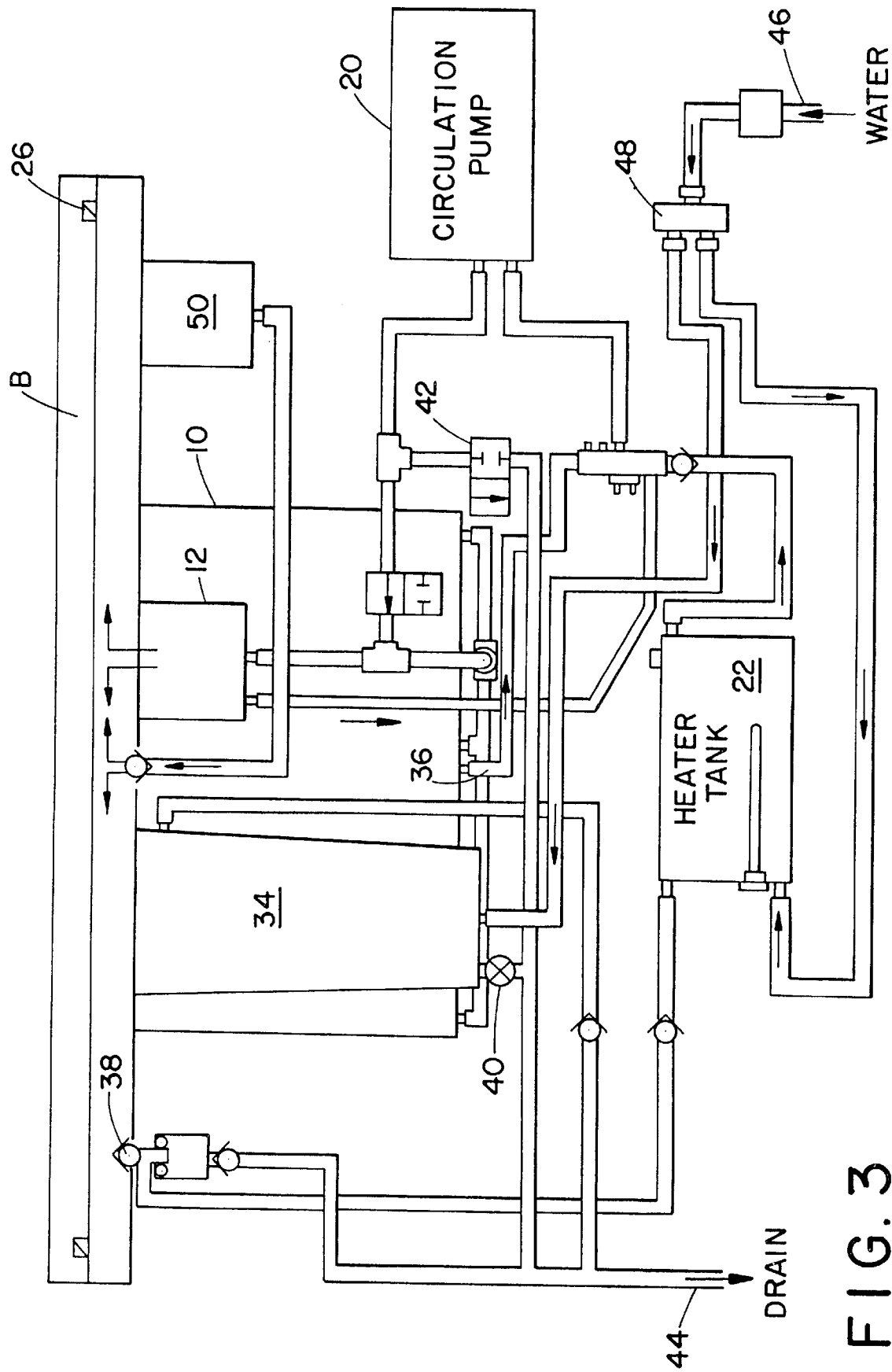
FIG. 3 is a plumbing diagram of the decontamination unit of FIG. 1.

With reference to FIGS. 1, 2, and 3, a microbial decontamination apparatus A is configured to sit on a countertop or other convenient work surface. A front door B is manually openable to provide access for inserting a tray or module C which holds, items to be microbially decontaminated and a cup or package D which holds a microbial decontaminant concentrate. More specifically, the items to be microbially decontaminated are located into the tray or module C which is slidably received in a microbial decontamination region, particularly a decontamination module receiving well 10. The items include surgical, medical, dental, mortuary, veterinary, and other items to be sterilized, disinfected, or otherwise microbially decontaminated.

As the cup or package D is loaded into a well 12, a knife assembly 14 severs and opens two compartments of the cup, releasing the contained microbial decontaminant concentrate. A circulation pump 20 circulates heated water from a heater tank 22 through the cup and the cup receiving well 12, dissolving the powdered reagents and forming a liquid sterilant, disinfectant, or other microbial decontamination fluid.

In the preferred embodiment, the inner and outer cups each contain one of an acid precursor and a persalt. More specifically to the preferred embodiment, the acid precursor is acetylsalicylic acid and the persalt is sodium or other perborates. These two compounds react in the presence of water to form sodium metaborate, peracetic acid, and salicylic acid. The volume of powdered ingredients is selected relative to the volume of water such that an anti-microbially effective concentration of peracetic acid is achieved. The sodium metaborate solution functions as an inorganic corrosion inhibitor. Preferably, additional corrosion inhibitors, buffers, and a wetting agent are added to these powders. Preferred copper and brass corrosion inhibitors include azoles, benzoates, other five-membered ring compounds, benzotriazoles, tolytriazoles, mercaptobenzothiazole, and the like. Other anti-corrosive buffering compounds include phosphates, molybdates, chromates, dichromates, tungstates, vanacdates, other borates, and combinations thereof. These compounds are effective for inhibiting steel and aluminum corrosion. For hard water in which calcium and magnesium salts may tend to precipitate, a sequestering agent such as sodium hexametaphosphate is also included. Other dry formulations can be utilized to generate chloride gas, hydrogen peroxide, hypochlorous acid, and other strong oxidants and agents which have a biocidal effect. Suitable anti-microbial fluids include gases such as ethylene oxide, vapors hydrogen peroxide or peracetic acid, gas plasmas and the like.

The microbial decontamination fluid flows out a front opening of the well 12 into channels 24 defined by projections 26 which mate with porous or non-porous portions of the lid B and valleys 28 in a face plate 30. The microbial decontamination fluid is channeled to receiving apertures 32 in the tray or module C and to a rinse liquid filter 34. The filter removes microbe and spores from the water or other rinse fluid sterilizing or disinfecting it. The anti-microbial solution which has flowed into and fills the tray or module C and the decontamination region 10 flows out an outlet 36 and is recirculated by the recirculation pump. As the water or other solution flows into the system to form the anti-microbial solution, a one-way vent 38 in the space between the front door B and the face plate 30 allows air and excess microbial solution to be removed.

After the items in the cartridge have been sterilized, disinfected, or otherwise decontaminated, valves 40, 42 are opened such that the sterilant or decontamination solution is drained through a drain 44. Water from an inlet 46 is either channeled by an inlet valve 48 to the heater tank 22 to start another cycle, or conveyed to the rinse fluid filter 34 to be sterilized or otherwise microbially decontaminated. The filter removes particulates, bacteria, spores, and other pathogenic life forms and contaminants from the incoming water by size. By selecting the filter fine enough to remove all pathogenic life forms, a sterile rinse water or solution is created and circulated out an open end of the rinse filter and through the paths 24 defined between the cover B and the face plate 30. Other filters, anti-microbial means such as high intensity UV light, and the like, may be substituted for filter 34 to treat the rinse water. This rinse fluid is again channeled through the module C and recirculated through the system. The rinse fluid is discharged through the drain 44 either at the end of a rinse cycle or continuously as new rinse fluid is introduced. At the end of the rinse cycle, the rinse fluid is replaced with air which flows through a microbe removing filter 50 into the space between the cover and the face plate.

In this manner, the sterilant or other anti-microbial solution sterilizes or microbially decontaminates the rinse fluid sterilizing filter and all paths, passageways, and surfaces downstream from the filter 34. This sterilization of all surfaces prevents sterile rinse fluid from flowing over any surface which was not sterilized or microbially decontaminated during the sterilizing or anti-microbial portion of the cycle.

Figure 4:
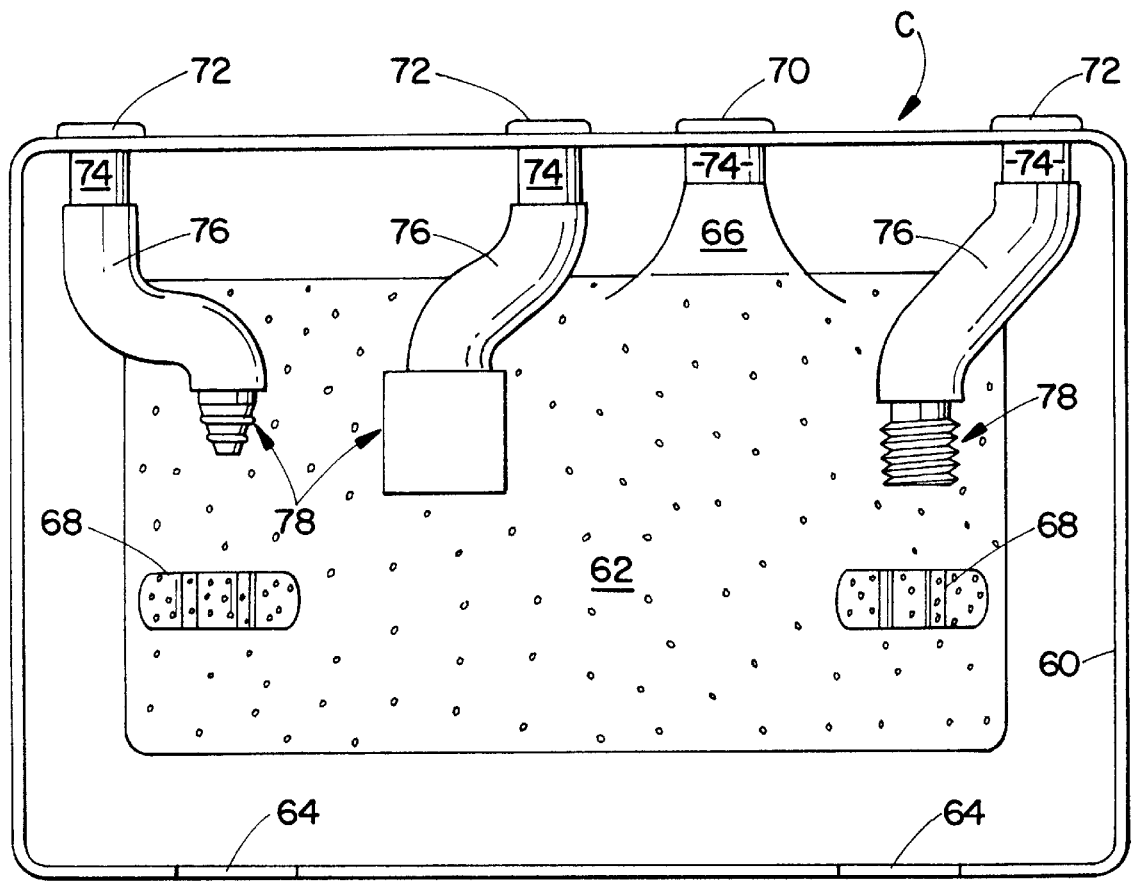
FIG. 4 is a top view of a bottom portion of the tray or module for holding the items to be microbially decontaminated.

With reference to FIG. 4, the tray or module C includes a lower portion that has a peripheral wall 60 extending peripherally around a base wall having a porous section 62. An upper or cover portion (not shown) closes the open top of the lower portion. The porous section 62 is large enough that the item or instruments supported in the tray rest on the porous section to reduce the potential for microbes to be trapped between the item during the decontamination cycle. After the decontamination cycle, the tray with the cover still closed can be used to store the sterilized items. The porous section permits water vapor to escape but is sufficiently tortuous that ambient microbes are blocked from penetrating. The peripheral wall 60 includes recessed regions 64 which permit fluid received in apertures 32 in the top or cover portion (not shown in FIG. 4) of the module or tray to be received freely in the interior. The bottom wall includes a depressed portion 66 defining the lowest portion of the bottom wall in connection with a drain aperture. Optionally, an elastomeric grommet or other connector 70 provides a fluid tight seal between the drain aperture and the return line 36 to the circulation pump. The bottom wall supports spring clamps 68 or other structures for retaining the items at selected locations in the tray. To eliminate the potential for microbes to be trapped in between the item and the retaining structure, the retaining structure is constructed of a porous construction.

The anti-microbial solution under pressure from the recirculation pump 20 is received through analogous elastomeric grommets or other connectors 72 at a rear face of the side wall 60. Check valves 74 permit the anti-microbial solution under pressure to enter and drain, but close when the pressure is removed to prevent microbial contamination from entering the module C after the decontamination process is complete. Tubing members 76 are connected with the check valve for directing the anti-microbial solution under pressure to fitting or attachment means 78. The tubing members 76 may be lengths of flexible tubing to facilitate easy interconnection with any of a multiplicity of items which contain internal passages to be decontaminated. Where appropriate to the nature of the item being microbially decontaminated and the item retaining structures or clamps 68, the tubing 76 may be rigid or less flexible. For example, the fluid which passes through the check valve 74 may be connected with a manifold tube having a larger multiplicity of nozzles and fitting means 78.

Figure 5:
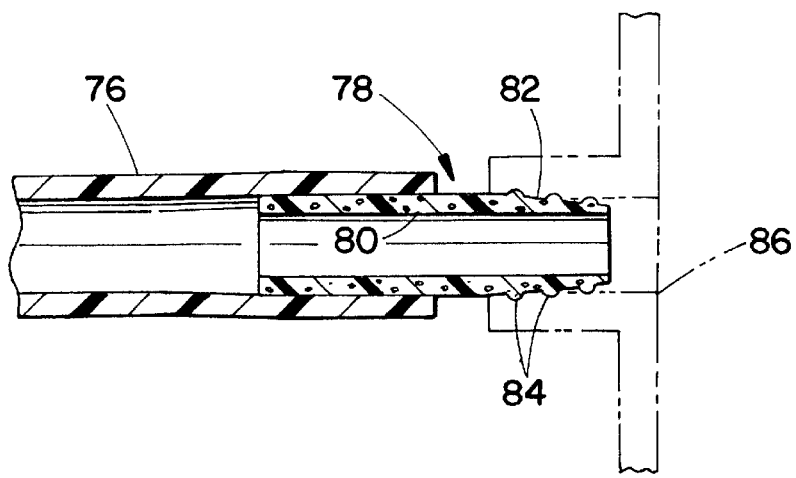
FIG. 5 is a cross-sectional view of one embodiment of a fitting in accordance with the present invention.

Various types of fitting means 78 are contemplated. With reference to FIG. 5, the fitting means 78 is an internal connector adapted to be inserted within an access port to an internal passage in the item. A sleeve of porous material 80 is fused or otherwise connected with the tubing member 76. The porous fitting 80 has a tapered end 82 to facilitate insertion into the port and resilient compression to form a firm frictional connection. Optionally, ribs 84 of the porous plastic material may be provided to improve the physical interconnection between the access port of the item 86.

With reference to FIG. 6, the hose 76 is fused or otherwise connected with a porous, fitting 78. The porous fitting 78 is sufficiently resilient to be received frictionally over a connection means on the item 86, such as a ribbed nipple. The fitting 78 again includes a porous sleeve 80 which contacts the item. A non-porous covering 90 jackets all or part of the porous sleeve to protect the more fragile sleeve to facilitate manual handling.

With reference to FIG. 7, the hose 76 is connected with a rigid porous member 92 into which threads 94 have been formed. The threads 94 have an appropriate diameter and pitch to match a threaded connector 96 on the item to be decontaminated.

The fitting-means illustrated in FIGS. 5–7 are exemplary of the numerous porous fittings that may be provided to match the requirements of the items being sterilized, disinfected, or otherwise microbially decontaminated. Suitable porous materials include expanded polyethylene, expanded Teflon, expanded nylon 6, porous ceramics, porous sintered metals, and the like. Other suitable polymers include nylon, polysulfone, polycarbonate, polyphthalate carbonate, polytetrafluoroethylene, polyvinylideneflouride, polyetherimide, styrene-butadiene copolymer, polyphenylene oxide, polypropylene and the like. In the preferred embodiment in which the sterilant solution includes a strong oxidant or acid, it is preferred that the fitting be sintered titanium or stainless steel or expanded plastic materials which have a strong oxidation or acid resistance. Normally available 3 to 25 micron pore sizes for the porous material have been found to provide sufficient flow of a liquid sterilant solution therethrough to achieve sterilization, disinfection, or microbial decontamination of the contacting surface of the item being sterilized. Of course, larger pore *sizes will provide greater anti-microbial fluid flow. Longitudinally extending passages, spiral passages, bores, and the like may be provided through or on the item contacting surface of the porous material to promote yet greater fluid flow.

Figure 8A:
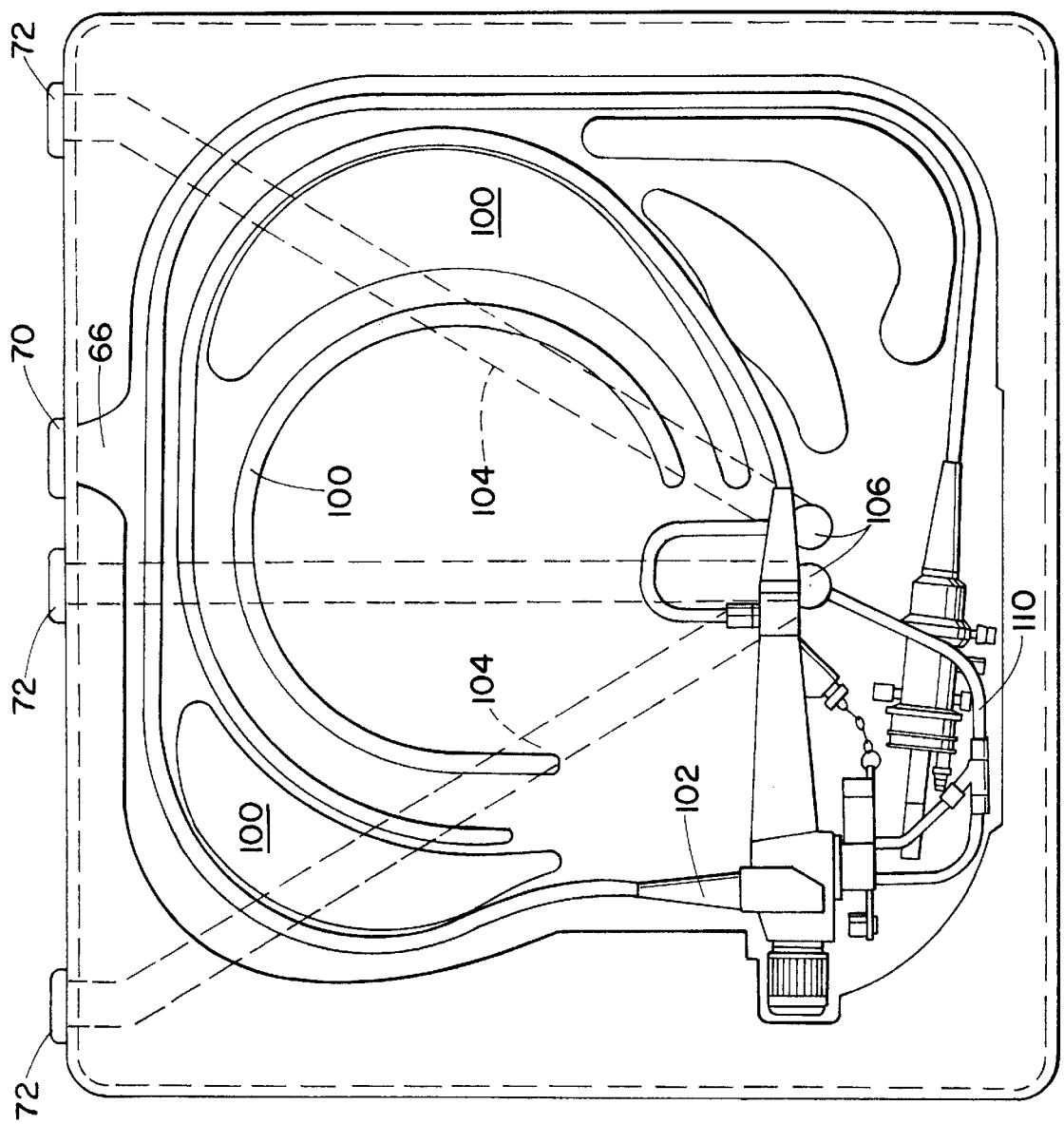
FIG. 8A is a top view of a tray holding an endoscope.
Figure 8B:
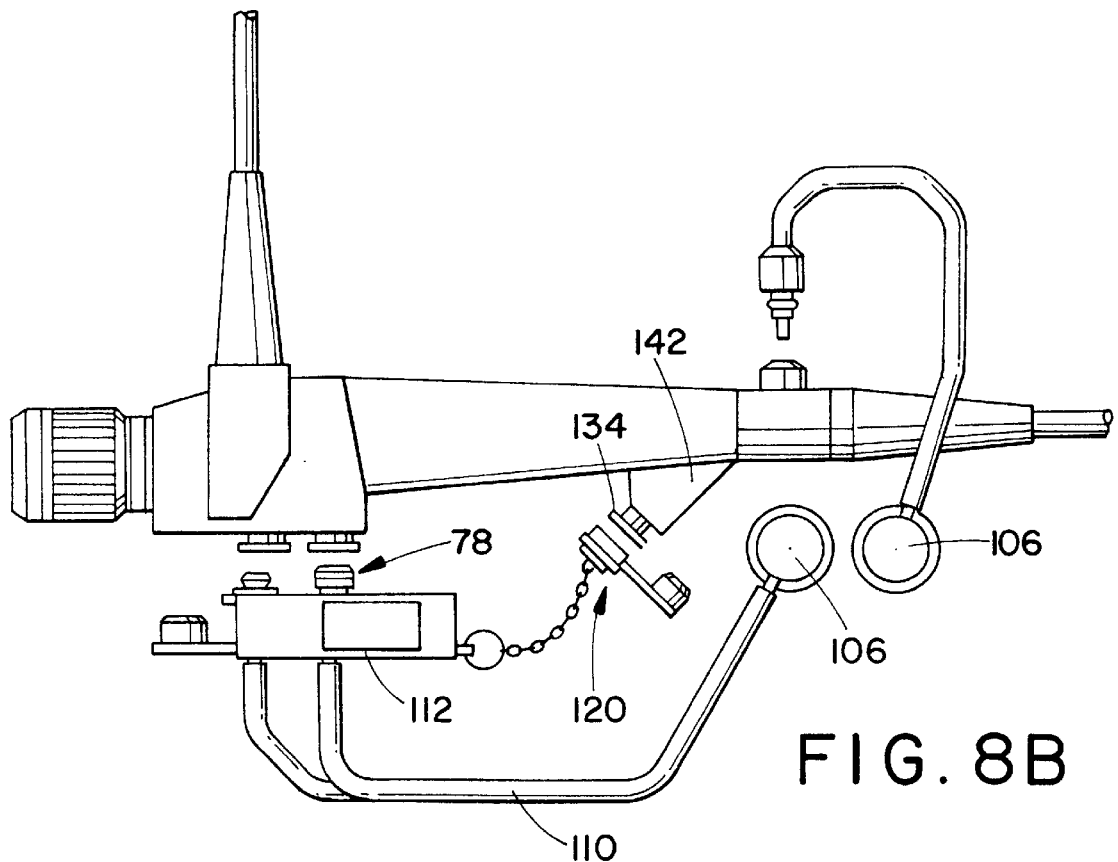
FIG. 8B is a detailed view of fittings and closures for one portion of the endoscope of FIG. 8A.
Figure 8C:
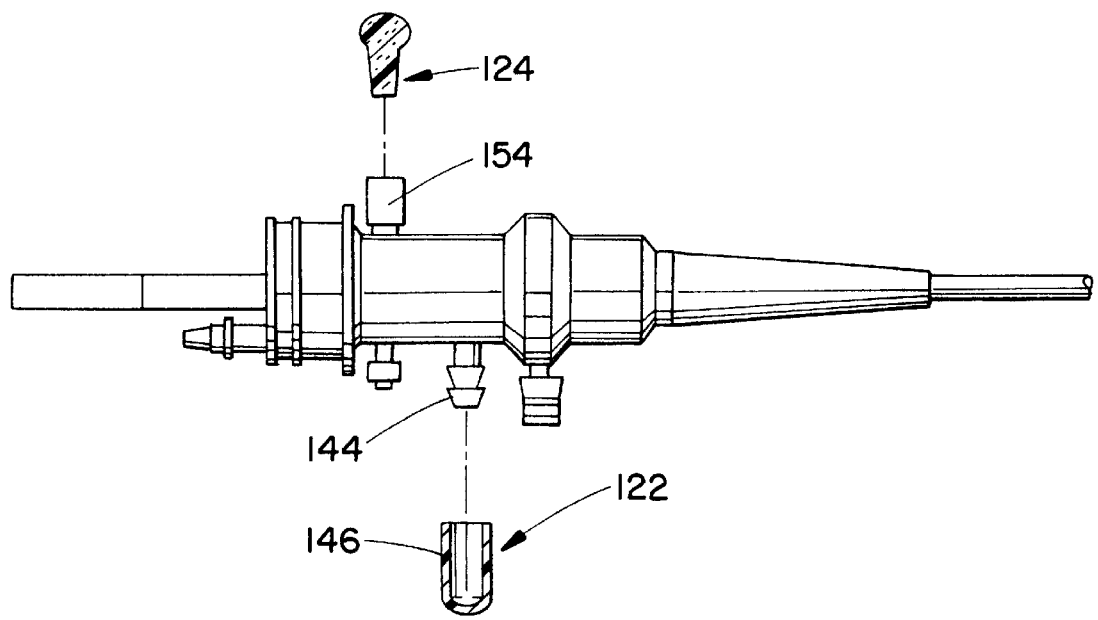
FIG. 8C is a detailed view of porous closures for another portion of the endoscope of FIG. 8A.

With reference to FIGS. 8A, 8B, and 8C, a plurality of upward projections or islands 100 which are either integrally formed with the bottom wall of the module C or as part of the insert to the tray or a decontamination chamber as shown in U.S. Pat. No. 5,077,088. The projections 100 define a plurality of passages which facilitate the ready receipt of the tubular elements of an endoscope 102 or the like. It is to be appreciated, that there are numerous different types of endoscopes and manufacturers of endoscopes, which results in endoscopes having a large number of different tubes, tubing lengths, fittings, and the like. The inlet grommets or fittings 72 are connected with fluid passages 104 extending under the lower surface of the tray to connectors 106. The connectors 106 include receptacles for receiving a plug attached to associated tubing unit 110. The plug opens a check valve in the connector as it is inserted to a receiving socket in the connector allowing fluid to pass through the connector 106 and the associated tubing 110. Although the plugs and the sockets are standardized, various tubing arrangements are contemplated in order to accommodate the wide variety of available endoscopes.

With reference to FIG. 8B, each of the tubing members 110 is connected with a fitting means 78. The fitting means 78 are of the porous material construction described above. Optionally, a manifold means 112 may support a plurality of fitting means 78. The plurality of fittings have a preselected spacing or relationship to provide for easier manual insertion of the fitting means to provide appropriate relative flow restriction such that each fitting means receives an appropriate portion of the flow for the endoscope in question, or the like.

With reference to FIGS. 8B and 8C, in order to ensure the proper flow of the sterilant solution various passages of the endoscope, porous caps 120, 122 or porous plugs 124 are inserted in various other access ports to the internal passages.

With reference to FIG. 9, the cap 120 includes a resilient porous member 130 with an internal bead or ridge 132 which snaps over a flange 134 at the access port. A collar of non-porous plastic 136 provides an interconnection 138 with a chain member 140 that connects the cap with the manifold means 112. The porous cap reduces a potential for air to be trapped in a dead end region 142 of the endoscope. Rather, any trapped air and a limited flow of the sterilant solution flows through the cap allowing the trapped air to escape, and bringing sterilant solution in contact with the interior and exterior surfaces of the flange 134.

With reference to FIG. 10, the cap 122 is constructed of a porous, elastomeric material that has sufficient resilience and elastic memory to be frictionally received on a nipple 142 or the like. In order to ensure adequate flow through nipple 142, the porous cap 122 has an aperture 144 therein. The aperture 144 is sufficiently restricted that only a limited portion-of the sterilant solution flowing through the interior passages is permitted to escape through it. As illustrated in the other embodiments, there are many applications for which the porous material provides adequate flow without an aperture.

With reference to FIG. 11, in another embodiment, the plug 124 includes an insertable porous portion 150 and an extended handle portion 152 to facilitate manual insertion and removal of the plug. In the illustrated embodiment, the handle portion 152, is constructed of a non-porous plastic material which is fused or otherwise connected to the porous plastic portion 150. The porous portion 150 is tapered to facilitate receipt into an access port 154 on the endoscope. The taper is such that at least a portion of the porous material is exposed above the access port 154 to provide a passage for any air trapped in the access port 154 to escape, preventing air blocks. The porous material permits the sterilant solution to flow between the plug and the inner surface of the access port 154, sterilizing or otherwise microbially decontaminating the contiguous interior surface. Optionally, a passage 156 may be defined within the plug to provide a shorter distance through the porous material through which the sterilant fluid and any trapped air must flow. Alternately, the entire plug, including the handle portion, can be of porous material.

Numerous other caps, plugs, and other termination devices as may be appropriate to the access port to the interior passages to be closed or restricted are contemplated. Again, internally or externally threaded plugs and caps may be provided. The plugs or caps may have ribs to facilitate frictional engagement in the port, channels on the surface, or bores therethrough to facilitate fluid flow along the contiguous surface of the item around the port.

With reference to FIG. 12, the cap or plug may be a small, one-piece porous plug or button 160. The simple button construction can be manufactured sufficiently cheaply that the plug can be kept in the endoscope or other equipment until ready for use. The porous nature of the plug would inhibit microbes from contaminating the internal passages. The plugs may be thrown away at the site of endoscope use or could be retained to be used the next time the endoscope is microbially decontaminated.

Figure 13:
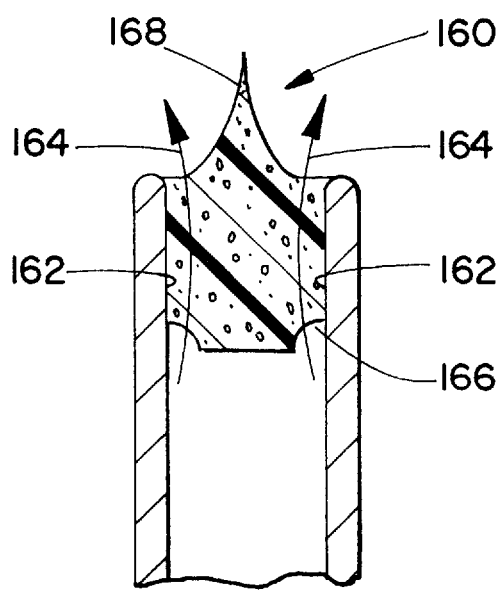
FIG. 13 is a cross-sectional view of another alternate embodiment of a plug in accordance with the present invention.

With reference to FIG. 13, the porous termination device 160 is configured to direct fluid flow primarily to the surface 162 to be decontaminated. Because fluid flows along the path of least resistance, the termination device has the least resistance around the edge and the most in the center. Shorter fluid flow path 164 are provided along the edges. The path length along the edges can be shortened by a cutout 166. Resistance along the center can be increased by a structure 168 that lengthens the flow path or increases the resistance. In the illustrated embodiment, the element 168 also serves as a handle portion. Other resistance increasing structures of porous and non-porous material can also be connected to the central portion of the plug.

Figure 14:
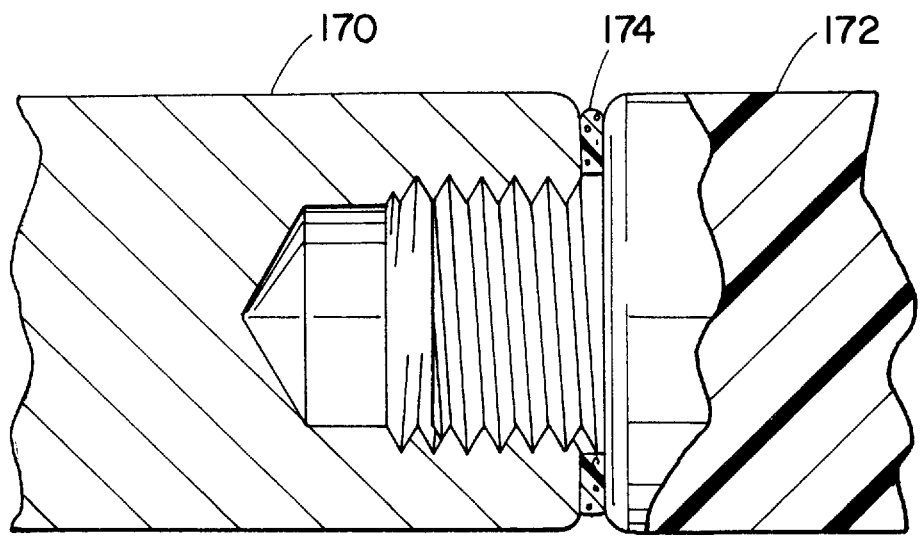
FIG. 14 is a cross-sectional view illustrating placement of porous material in crevice regions of instruments to promote anti-microbial fluid flow.

With reference to FIG. 14, rather than constructing connectors of porous material, parts of the medical equipment can be constructed of porous material. The porous material can be located adjacent connectors or other abutting parts. Some medical instruments and other items to be microbially decontaminated have parts 170, 172 which are clamped or anchored together. However, the surfaces which do not mate perfectly define a thin crevice that is large enough to hold microbes, yet thin enough to inhibit anti-microbial fluid flow. To assure anti-microbial fluid flow or penetration into the crevice, the item is manufactured with a thin piece 174 of the porous material in the crevice. Porous material can be used analogous to gaskets, as segments in dead end branches to assure fluid flow during sterilization, and the like.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. In a microbial decontamination system for killing microbes on surfaces of an item by immersing the item in an anti-microbial fluid, the item having at least two interconnected pieces that are connected together such that surfaces on the connected pieces abut each other defining a crevice in which microbes might become trapped, THE IMPROVEMENT COMPRISING:

a porous portion disposed in the crevice, which porous portion is sufficiently porous that the anti-microbial fluid penetrates therethrough to contact and kill the microbes hidden between and on the abutting surfaces.

2. In the microbial decontamination system as set forth in claim 1, the improvement further comprising:

one of the item pieces having a threaded bore and the other of the item pieces having a threaded member which is threadedly received into the threaded bore; and, the porous portion being a washer which is disposed around the threaded bore.

3. In the microbial decontamination system as set forth in claim 1, the improvement further comprising:

the item having at least one internal passage and a bore in fluid communication therewith;

a porous fitting frictionally received in the bore.

4. A microbial decontamination system comprising:

a microbial decontamination region for receiving an item to be microbially decontaminated;

an anti-microbial fluid inlet through which anti-microbial fluid is introduced into the microbial decontamination region;

a fluid outlet through which anti-microbial fluid and spent anti-microbial fluid is removed from the microbial decontamination region;

the item having at least two interconnected pieces that are connected together such that surfaces on the connected pieces abut each other defining a crevice in which microbes may become trapped;

an associated surface which abuts one of the potentially microbially contaminated surfaces such that microbes can be sheltered therebetween, avoiding contact with the anti-microbial fluid;

a porous structure disposed in the crevice, the porous structure being permeable by the anti-microbial fluid such that the anti-microbial fluid permeates therethrough contacting and killing any microbes hidden between and on the abutting surfaces.

5. The microbial decontamination system as set forth in claim 4 wherein the associated surface is a surface of a support structure on which the item is supported.

6. The microbial decontamination system as set forth in claim 4 wherein the associated surface is a surface of a spring clamp within which the item is clamped to hold it securely against movement in the decontamination region, porous structures being disposed between all portions of the spring clamp which contact surfaces of the item.

7. The microbial decontamination system as set forth in claim 6 wherein the spring clamp is constructed of an open-celled, resilient plastic material such that the spring clamp and the porous structure are integral.

8. A microbial decontamination system comprising:

a microbial decontamination region for receiving an anti-microbial fluid and an item to be microbially decontaminated, the item being constructed of at least two pieces, an associated surface being defined on one piece of the item abutting another surface of the item that is potentially contaminated by microbes such that a microbe shielding crevice is defined therebetween;

a porous structure including a porous element disposed between the associated surface and the potentially microbially contaminated surface, the porous structure being permeable by the anti-microbial fluid such that the anti-microbial fluid permeates therethrough contacting the potentially microbially contaminated surface killing any microbial contamination thereon.

9. A microbial decontamination system comprising:

a construction for holding an item to be microbially decontaminated, the construction including:

an anti-microbial fluid inlet, a fluid outlet, an ambient microbe block for preventing airborne microbes from entering the inlet and the outlet, a spring clamp anchored to the construction, the spring clamp having opposing fingers which are spring-biased together to engage surfaces of the item to be decontaminated securely and releasably therebetween, wherein the opposing fingers of the spring clamp are constructed of a rigid, porous material such that the porous portions are integral with the opposing fingers, wherein the porous portions are permeable by anti-microbial fluid, which porous portions of said spring clamp fingers abut and contact the item to be microbially decontaminated;

a circulation system for inundating the construction with anti-microbial fluid, the porous portions of the spring clamp fingers being permeable by the anti-microbial fluid such that the anti-microbial fluid penetrates the porous portions of the spring clamp fingers and reaches the surfaces of the item that are engaged between the porous portions 6f the spring clamp fingers.

10. The microbial decontamination system as set forth in claim 9 wherein the rigid, porous material is a rigid, open-celled plastic material.

* * * * *